US012788315B2

(12) United States Patent
Bonificio et al.

(10) Patent No.: US 12,788,315 B2
(45) Date of Patent: Nov. 10, 2026

(54) WEARABLE RING DEVICE AND METHOD OF MONITORING SLEEP APNEA EVENTS

(71) Applicant: APNIMED, INC. (DELAWARE), Cambridge, MA (US)

(72) Inventors: William D. Bonificio, Watervliet, NY (US); Lawrence G. Miller, Cambridge, MA (US); Dennis Molnar, Hopkinton, NH (US); D. Andrew Wellman, Wayland, MA (US)

(73) Assignee: APNIMED, INC. (DELAWARE), Cambridge, MA (US)

( * ) Notice: Subject to any disclaimer, the term of this patent is extended or adjusted under 35 U.S.C. 154(b) by 144 days.

(21) Appl. No.: 18/286,169

(22) PCT Filed: Apr. 14, 2022

(86) PCT No.: PCT/US2022/024747

§ 371 (c)(1),
(2) Date: Oct. 9, 2023

(87) PCT Pub. No.: WO2022/221487

PCT Pub. Date: Oct. 20, 2022

(65) Prior Publication Data

US 2024/0188881 A1 Jun. 13, 2024

Related U.S. Application Data

(60) Provisional application No. 63/175,070, filed on Apr. 15, 2021.

(51) Int. Cl.

*A61B 5/00* (2006.01)
*A61B 5/024* (2006.01)
*A61B 5/1455* (2006.01)

(52) U.S. Cl.

CPC .......... *A61B 5/4818* (2013.01); *A61B 5/0002* (2013.01); *A61B 5/02405* (2013.01);
(Continued)

(58) Field of Classification Search

CPC .. A61B 5/4818; A61B 5/6826; A61B 5/02416
See application file for complete search history.

(56) References Cited

U.S. PATENT DOCUMENTS 6,608,562 B1 8/2003 Kimura et al.
10,918,289 B1 2/2021 Wasson
(Continued)

FOREIGN PATENT DOCUMENTS

JP 5562805 B2 7/2014
WO 2015146512 A1 10/2015

OTHER PUBLICATIONS

PCT/US2022/024747 International Search Report dated Aug. 9, 2022.

*Primary Examiner* — Tammie K Marlen
(74) *Attorney, Agent, or Firm* — Honigman LLP

(57) ABSTRACT

A health monitoring system includes a band that is wearable on a user's extremity, such as a finger. A pulse oximetry sensor is disposed at an inner surface of the band and is configured to collect data representative of the heart rate and blood oxygen level of the user. An electronic control unit (ECU) is connected to the pulse oximetry sensor. When the band is worn by the user, the pulse oximetry sensor collects heart rate and blood oxygen level data and transmits the collected data to the ECU. The ECU receives the collected data from the pulse oximetry sensor, processes the collected data, and stores the processed data at a time interval, such as every 3 seconds or less. When the band is removed from the user, the ECU transmits the processed data stored in the storage unit to a remote device.

29 Claims, 11 Drawing Sheets

(52) U.S. Cl.
CPC ........ *A61B 5/14551* (2013.01); *A61B 5/6826* (2013.01); *A61B 5/6843* (2013.01)

(56) References Cited

U.S. PATENT DOCUMENTS

| | | | | |
|---|---|---|---|---|
| 2010/0168531 | A1 | 7/2010 | Shaltis et al. | |
| 2014/0275852 | A1 | 9/2014 | Hong | |
| 2014/0378777 | A1 | 12/2014 | Conrad et al. | |
| 2016/0066827 | A1 * | 3/2016 | Workman | A61B 5/742 600/340 |
| 2018/0120892 | A1 | 5/2018 | Von Badinski et al. | |
| 2019/0134396 | A1 * | 5/2019 | Toth | A43B 3/34 |

* cited by examiner

WEARABLE RING DEVICE AND METHOD OF MONITORING SLEEP APNEA EVENTS

CROSS-REFERENCE TO RELATED APPLICATIONS

This application is a National Stage Application and claims priority under 35 U.S.C. § 371 to Patent Cooperation Treaty application PCT/US2022/024747, filed Apr. 14, 2022, which claims the benefit of and priority under 35 U.S.C. § 119(e) to U.S. Provisional Application No. 63/175,070, filed Apr. 15, 2021. Priority is claimed to each of these applications and the disclosures of these prior applications are considered part of the disclosure of this application, and to the extent allowed, the entire contents of the aforementioned applications are incorporated herein.

TECHNICAL FIELD

The present disclosure relates to pulse oximetry sensors, and more particularly to a wearable ring device and method of screening, monitoring, diagnosing and detecting sleep apnea.

BACKGROUND

It is known to provide various sensors in a user wearable device to collect and track health data for a user wearing the device. Devices commonly collect data representative of a user's heart rate, blood oxygen levels, and physical movement. Additionally, wearable health trackers are commonly used in the medical setting, such as during polysomnography, for purposes of diagnosis and patient monitoring. Polysomnography, commonly referred to as a sleep test, is frequently used to diagnose sleep apnea.

SUMMARY

The present disclosure provides a health monitoring system that includes a wearable band or ring device with a pulse oximetry sensor disposed at the inner surface of a band worn around a user's extremity, such as a finger band around a user's finger or wrist. When the band is worn by a user, the pulse oximetry sensor uses light transmittance through the user's extremity to collect data representative of the heart rate and blood oxygen level of the user at a time interval, such as every 3 seconds or less or every 2 seconds or less or every 1 second or less. The sensor transmits the collected data to an electronic control unit (ECU), which may be disposed onboard the sensing band, on another connected wearable device, or otherwise on a remote device. The ECU processes the collected data via a data processor and stores the processed data at a storage unit. After a duration of time where the ECU has stored processed data, such as after a monitored event or sleep event, the ECU may transmit the processed data stored at the storage unit to another wearable or remote device via a transmitter. The remote device can operate to further process the received data and display the further processed data, such as to correlate or compare the monitored event with past or related information. Thus, the collected data can be processed and analyzed for purposes of screening, detecting, diagnosing, or monitoring sleep apnea.

The pulse oximetry sensor of the wearable band device may include light sources and optical sensors on opposing sides of the band so as to collect blood oxygen and heart rate data of the user via transmittance through the user's extremity. Also, the wearable band device may include a self-contained battery that operates the pulse oximetry sensor and corresponding ECU, so that the user can wear and operate the device without a wired connection to an accessory device or power source. The wearable band device collects data during a monitored event at a rapid time interval, such as every 1 or 2 or 3 seconds or less, processes the collected data, and stores the processed data in substantially the same rapid time interval. The wearable band device provides highly accurate readings and provides reliable retention of the sensor at the body of the user. Thus, the wearable band device provides an improved method of screening, detecting, monitoring, and analyzing blood oxygen levels and heart rates of users over extended periods of time, such as during sleep events or generally overnight.

According to one aspect of the present disclosure, a health monitoring system includes a finger band having an inner surface configured to at least partially surround a finger of a user. A pulse oximetry sensor disposed at the inner surface of the finger band is configured to collect data representative of the heart rate and blood oxygen level of the user. An electronic control unit (ECU) is disposed at the finger band and connected to the pulse oximetry sensor. The ECU includes electronic circuitry and associated software. The electronic circuitry includes a data processor, a storage unit, and a transmitter. When the finger band is worn by the user during a sleep event or overnight, the pulse oximetry sensor collects data representative of the heart rate and blood oxygen level of the user and transmits the collected data to the ECU during the sleep event or overnight. When the finger band is worn by the user during the sleep event or overnight, the ECU receives the collected data from the pulse oximetry sensor, processes the collected data with the data processor, and stores the processed data in the storage unit at a time interval of every 2 seconds or less. When the finger band is removed from the user after the sleep event or overnight, the ECU transmits the processed data stored in the storage unit to a remote device via the transmitter using Bluetooth, wifi, a wire or another means of rapidly transmitting data.

Implementations of the disclosure may include one or more of the following optional features. In some implementations, the pulse oximetry sensor includes a light emitter disposed at a first location at the inner surface of the finger band and a light detector at a second location at the inner surface of the finger band remote from the first location. The light emitter, when electrically powered, directs a beam of light along a radial path and the light detector is located at the second location within the radial path. In some implementations, the pulse oximetry sensor collects data representative of the heart rate and blood oxygen level of the user at a time interval of every 1 second or less. In some examples, the pulse oximetry sensor collects data representative of the blood oxygen level of the user responsive to collecting data representative of the user or at a time interval representative of a heart rate of the user, such as an average heart rate of the user. In some implementations, the pulse oximetry sensor collects data representative of the blood oxygen saturation at a frequency of greater than or approximately 1 Hz, greater than 0.75 Hz, greater than 0.50 Hz, or greater than 0.25 Hz.

In some implementations, a sensor disposed at the wearable band device, such as the pulse oximetry sensor, senses when the band is being worn by the user and, responsive to the sensor sensing that the band is being worn by the user, the pulse oximetry sensor begins collecting data representative of the heart rate and blood oxygen level of the user and transmitting the collected data to the ECU during the sleep event. In some implementations, after the sleep event, a sensor disposed at the band, such as the pulse oximetry sensor, senses that the band is not being worn by the user and, responsive to sensing that the band is not being worn by the user after the sleep event, the ECU transmits the processed data stored in the storage unit to the remote device via the transmitter. Furthermore, some implementations of the ring device include an actimetry sensor disposed at the band to collect data representative of movement of the user, such as to transmit the collected movement data to the ECU during the sleep event to be processed with the collected data representative of the blood oxygen level and heart rate of the user. In some implementations, the signals from the actimetry sensor may also or alternatively indicate that a sleep event has stopped or started.

According to another aspect of the present disclosure, method for measuring health data includes providing a wearable band device to be worn by a user during a sleep event or overnight. The band includes a pulse oximetry sensor disposed at an inner surface of the band and an ECU connected to the pulse oximetry sensor. While the band is worn by the user during the sleep event, the method includes collecting data representative of the blood oxygen level and heart rate of the user via the pulse oximetry sensor at a time interval of every 2 seconds or less and transmitting the collected data to the ECU. While the band is worn by the user during the sleep event and responsive to receiving the collected data at the ECU, the method further includes processing the collected data via a data processor of the ECU and storing the processed data at a storage unit of the ECU. The method further includes, after the finger band is removed from the user following the sleep event, transmitting the processed data stored at the storage unit to a remote device via a transmitter of the ECU using Bluetooth, wifi, a wire or another means of rapidly transmitting data.

This aspect may include one or more of the following optional features. In some implementations, the ECU is disposed at the wearable band device or remote from the band, such as at the remote device. In some implementations, the pulse oximetry sensor collects data representative of the blood oxygen level of the user at a time interval representative of the heart rate of the user. Furthermore, processing the collected data can include calculating a hypoxic burden value.

The details of one or more implementations of the disclosure are set forth in the accompanying drawings and the description below. Other aspects, advantages, purposes, and features will be apparent upon review of the following specification in conjunction with the drawings.

BRIEF DESCRIPTION OF THE DRAWINGS

Like reference symbols in the various drawings indicate like elements.

DETAILED DESCRIPTION

Figure 1A:
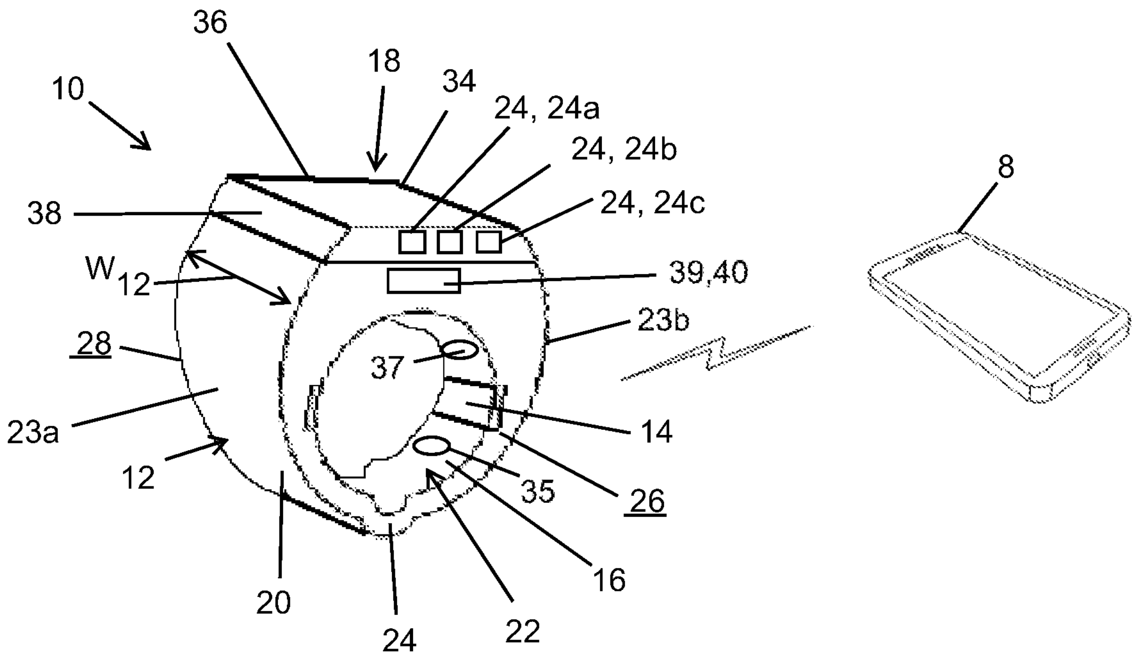
FIG. 1A is a perspective view of a wearable ring device wirelessly connected to a mobile device.

Referring now to the drawings and the illustrative examples depicted therein, a health monitoring system is shown that includes a band or ring device 10 that is wearable by a user and that is wirelessly connectable to another remote device 8, such as a wearable device (e.g., a watch), a smart phone, personal computer, or wireless network. The wearable band or ring device 10 has a pulse oximetry sensor 14 disposed at a band 12 worn around a user's extremity, such as a finger band, wrist band, ankle band or the like. The band 12 of the ring device 10 is configured to at least partially surround a finger of a user and includes a pulse oximetry sensor 14 disposed at an inner surface 16 of the finger band 12. The pulse oximetry sensor 14 uses light transmittance through the user's extremity, including the user's skin and soft tissue. Using light transmittance, the pulse oximetry sensor 14 collects data representative of the heart rate and blood oxygen level of the user at a time interval, such as every 3 seconds or less or every 2 seconds or less or every 1 second or less.

The sensor transmits the collected data to an electronic control unit (ECU), which may be disposed onboard the wearable band device 10, on another connected wearable device, or otherwise on a remote device 8. The ECU may include circuitry for a data processor, a storage unit, and a transmitter disposed at the finger band and connected to the pulse oximeter 14, such as a wired connection when disposed at the finger band or another wearable device or a wireless connection when disposed at another wearable device or remote device. When the band is worn by a user for a duration of time, which may be referred to as a monitored event (such as a sleep event, overnight or a physical activity), the pulse oximetry sensor 14 collects data representative of the heart rate and blood oxygen level of the user and transmits the collected data to the ECU during the event. During the monitored event, the ECU may receive the collected data from the pulse oximetry sensor, process the collected data with the data processor, and store the processed data in the storage unit at a selected time interval. The selected time interval for storing collected and processed data may be every 3 seconds or less, 2 seconds or less, or 1 second or less to capture data capable of being analyzed with a high degree of accuracy during transient periods of the monitored event. After the monitored event (such as when the user wakes up or ceases physical activity), the ECU transmits the processed data stored in the storage unit to the remote device. Thus, the health monitoring system is configured to collect, process, and store data representative of a user's heart rate and blood oxygen level at a select time interval (such as every 2 seconds or less) throughout an event via the band device and, after the event, transmit the stored data to a remote device. As will become clear through the disclosure below, this health monitoring system is applicable in a number of different contexts and for various uses such as monitoring oxygenation levels of users or patients with various respiratory, pulmonary, and cardiovascular diseases and disorders or monitoring heart rate and oxygenation during physical activity. As discussed specifically herein, the health monitoring system and corresponding wearable ring device according to the present disclosure can benefit medical treatments, dosing, diagnosis, phenotyping, screening, and ongoing monitoring of sleep apnea and related symptoms and conditions.

Sleep apnea is a medical condition in which a person's breathing repeatedly stops and starts during sleep (known as apnea events), which can result in restless sleep, snoring, gasping for breath during sleep, and other sometimes serious issues caused by apnea events. There are multiple forms of sleep apnea, but the most common forms of sleep apnea are obstructive sleep apnea and central sleep apnea. Obstructive sleep apnea (OSA) occurs when throat muscles relax, collapsing the airways, whereas central sleep apnea occurs when the brain does not send proper signals to the muscles that control breathing. Apnea events range from mild to severe and last from about 10 seconds to 30 seconds or longer in length, meaning that a person's breathing may stop for upwards of 30 seconds or more multiple times during a single night's sleep. Apnea events do not always wake the person suffering from sleep apnea and thus sleep apnea can often go undetected and undiagnosed for a long period of time.

Traditionally, sleep apnea is diagnosed via polysomnography (commonly referred to as a sleep test or PSG), during which lab technicians monitor a patient during a full night of sleep via a suite of sensors, including oximeter sensors. Oximeter sensors, when worn by a user, measure the user's blood oxygen levels. During sleep, low blood oxygen levels can indicate an apnea event. Polysomnography also commonly measures a person's heart rate, brain waves, breathing, and eye and body movements to detect other indications of restless or interrupted sleep. Once a person is diagnosed with sleep apnea, they are typically prescribed a treatment such as a wearable breathing device (such as a CPAP machine with mask), an oral device that is placed in the mouth, or potentially a pharmacological remedy.

One problem associated with prescribing therapeutic drugs as a treatment for sleep apnea is the difficulty in achieving a correct dosage for the individual patient. After the patient begins taking medication, absence of apnea events can indicate that the drug is working as intended. However, it is often desirable to reduce medication dosing down to a minimum level necessary to prevent apnea events, such as to reduce side effects or reduce prescription costs. Monitoring the patient's blood oxygen levels and heart rate during sleep can indicate the occurrence (or absence), length, and severity of apnea events and thus can be a relatively simple way to measure the efficacy of the prescribed drug. However, tailoring a treatment to a particular patient often requires testing several different dosages or other adjustments, each for an extended period of time, before finding the right one. Furthermore, it is common to adjust a patient's dosage over time to maintain the optimal effectiveness of the medication in case the patient builds a tolerance or becomes sensitive to a medication side effect or loses weight and requires less medication/treatment. Additionally, many patient become less adherent to treatments over time. Thus, it is highly desirable to monitor a patient's blood oxygen levels and heart rate during sleep over an extended period of time while the patient is prescribed a treatment at different dosage levels or strengths to ensure the apnea events are being properly treated while working towards optimizing the treatment regimen.

Additionally, achieving as accurate of readings as possible of blood oxygen levels and heart rate during sleep is critical in properly tailoring optimal treatments. As apnea events become less severe, less frequent, and/or shorter in length, dips in blood oxygen levels (or other indicators of an apnea event) are less prevalent and require more precise measurements to detect. Polysomnography (PSG) and home sleep tests (HST) are highly effective methods for detecting acute apnea events, but because of all the intrusive equipment attached to patients' bodies these sleep studies do not always portray a patient's natural, every night sleep and are prohibitively expensive, and tailoring treatment requires accurate measurements over an extended period of time, they are an impractical way to monitor a patient after sleep apnea has been diagnosed. Instead, prescribing doctors often must rely solely on anecdotal evidence provided by the patient (such as via surveys or questionnaires related to symptoms) or less accurate in-home measuring devices (with pulse oximetry sensors) to gauge how well the patient is responding to the treatment.

Figure 10:
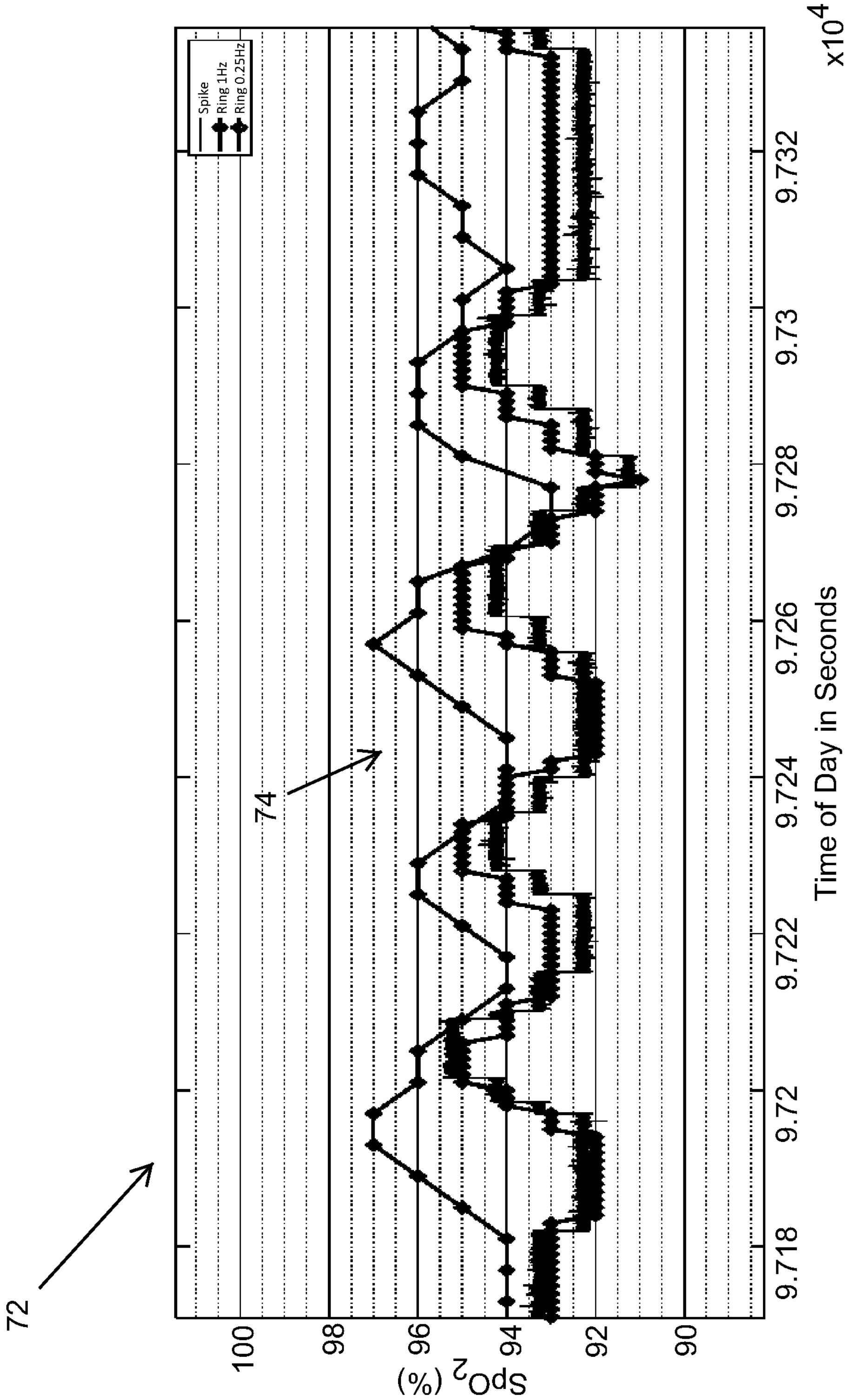
FIG. 10 is a graph comparing readings of a user's blood oxygen level over time collected using a fingertip oximeter device, a finger ring oximeter device recording oxygen saturation at a frequency of 0.25 Hz, and a finger ring oximeter device recording oxygen saturation at a frequency of 1 Hz.

For example, pulse oximeter devices known in the art may collect data representative of a user's heart rate and blood oxygen levels through techniques of reflectance or transmission. Pulse oximeter devices that measure using reflectance place a light emitter at the skin surface of a user (such as a wrist) and a light detector at the same skin surface a short distance away from the light emitter. Light emitted from the light emitter is reflected by the skin of the user and detected by the light detector to generate the desired readings. In contrast, pulse oximeter devices that measure using transmission place a light emitter at the skin surface of a narrow body part of a user and a light detector at the skin surface on the opposite side of the narrow body part (such as the top and bottom surfaces of a fingertip). Light emitted from the light emitter shines through the skin and soft tissue of the user's extremity and is detected by the light detector to generate the desired readings. Transmission devices generate more accurate readings than reflectance devices, but because transmission devices generally must clamp on to the user (or otherwise provide a retaining force), reflectance devices are generally more comfortable for the user. Thus, reflectance devices are often favored when a more accurate reading is not necessary, such as in smart watches or activity trackers, while transmission devices are more prevalently found in medical devices like fingertip pulse oximeters. However, due to the discomfort caused by the forceful retaining devices of transmission pulse oximeters and the fact that they are generally positioned at an outermost edge of a body part (such as a fingertip, ear lobe, or nare), they are often worn improperly, readjusted, taken off, or fall off during use, all of which cause inaccurate and/or incomplete data readings. The discomfort caused by clamping devices so that they stay on throughout the night can even make it difficult for users to fall asleep and stay asleep, as they can become painful to wear for hours at a time. Additionally, the clamping pressure of common transmission devices can result in altered or easily manipulated heart rate measurements (such as via movement or flexing of the finger). Furthermore, known devices also commonly record data at relative long time intervals, resulting in missed apnea events and/or an inability to accurately determine the severity or duration of an apnea event between recordings. For example, recording oxygen saturation at a frequency of 0.25 Hz is not as accurate as recording oxygen saturation at a frequency of 1 Hz and results in missed apnea events when patients with sleep apnea, such as shown in FIG. 10. The inaccuracy is true for apnea events that are both longer and shorter than 4 s duration. Overall, currently known methods of monitoring a person's heart rate and blood oxygen levels over an extended period of time are lacking in comfort for the user, security of the connection between the sensor device and user, accuracy of the data recorded, and the methods and calculations used to analyze data after it has been collected. These shortfalls present many issues, specifically in the at-home and laboratory sleep-monitoring settings.

A wearable band device 10 in accordance with the present disclosure provides a transmission pulse oximeter that is worn like a standard finger ring at an intermediary portion of the user's finger and retained thereat without a significant or noticeable clamping force. While the ring device 10 may fit snugly around the user's finger to ensure proper sensor readings, the ring device is more comfortable than a fingertip pulse oximeter and less susceptible to being inadvertently pulled off or shifted during use. The ring device's unique qualities help ensure that the ring device 10 is worn for the duration of a user's overnight sleep (referred to as a sleep event) and that the pulse oximetry sensor 14 will continue collecting accurate data throughout the duration of the data collecting period. Additionally, and as will be described further below, the device 10 collects, processes, and stores data at a high rate or frequency (such as every 2 seconds or less) to ensure accurate detection of apnea event occurrences and precise measurements as to the severity of the apnea events. Thus, the band device 10 processes the captured data to output sleep-apnea-focused data sets such as a hypoxic burden calculation. The band device 10 provides these accurate measurements and opportunity for sleep analysis that can be incorporated with polysomnography, such as relatively easy to conduct at-home sleep studies.

Figure 1B:
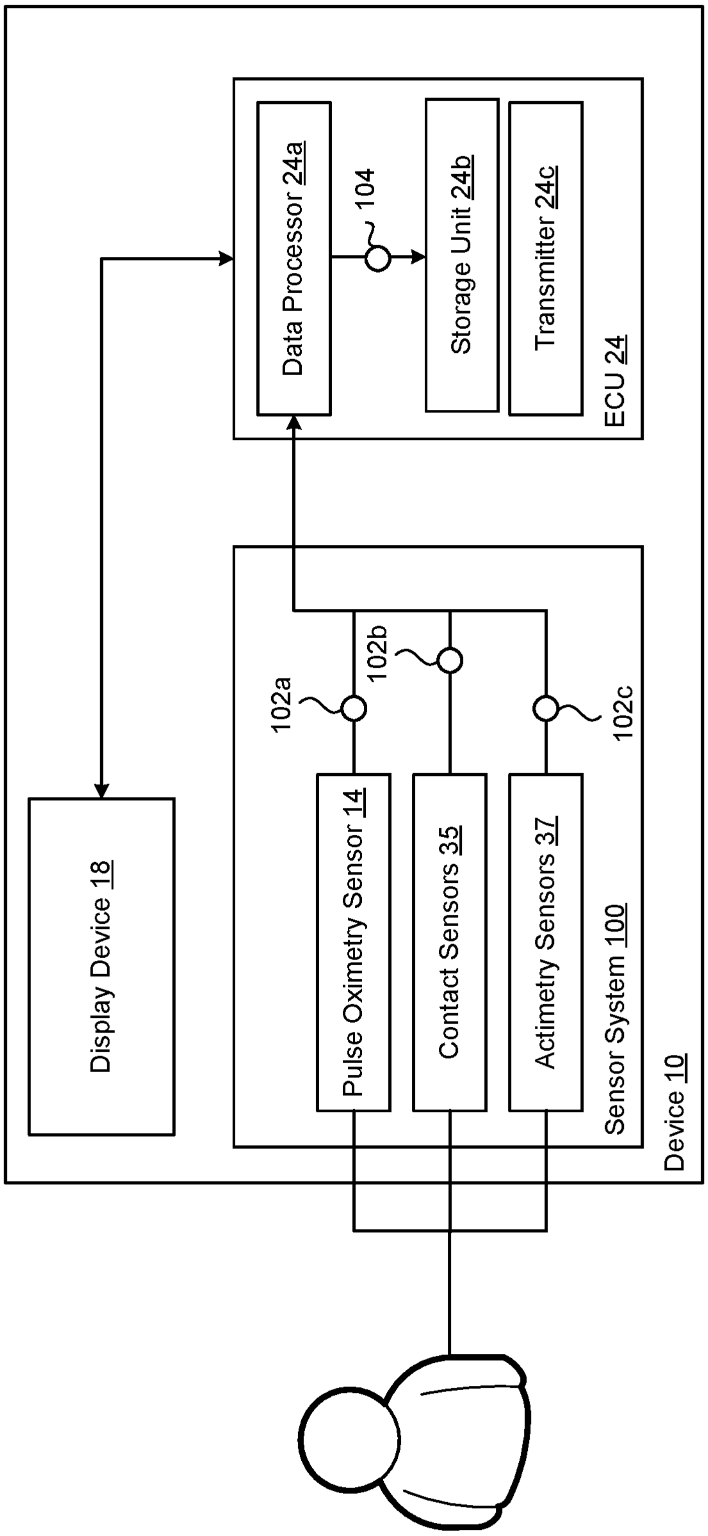
FIG. 1B is a schematic view of the wearable ring device of FIG. 1A.

In reference to FIGS. 1A and 1B, a health monitoring system is shown that includes a wearable band device 10 wirelessly connected to a mobile device such as a smart phone 8. The wearable device 10 includes a finger band 12, a pulse oximetry sensor 14, and a display device 18. The finger band 12 includes a flexible material, such as silicone, with an outer surface 20 and an inner surface 16. The inner surface 16 of the band defines an opening 22 or finger-receiving portion configured to receive a user's finger. As illustrated, the band 12 includes a first band portion 23*a* defining a first side of the opening 22 and a second band portion 23*b* formed on an opposite side of the band 12 and defining a second side of the opening 22.

Optionally, the band 12 may include an expansion feature 24 that enables the band 12 to accommodate different size fingers. In the illustrated example, the expansion feature 24 includes a U-shaped notch 24 that connects opposing distal ends of the first band portion 23*a* and the second band portion 23*b* at the lower portion of the opening 22. If a user places the ring device 10 on their finger and their finger is larger than the resting size of the band's inner surface, the portion of the band 12 forming the U-shaped notch 24 stretches to increase the size of the finger-receiving portion 22 to accommodate the larger finger. Although shown as a continuous ring with a U-shaped expansion notch 24 to accommodate differently sized fingers, the band 12 may also be a non-continuous ring of flexible material with a gap between the two portions 23*a*, 23*b* of the ring 12 comprising the expansion feature. In those embodiments, when a finger larger than the resting size of the finger band 12 is inserted into the ring device 10, the two side portions 23*a*, 23*b* of the band 12 flex outwards to accommodate the larger finger. In further examples the band may be a rigid material, such as metal or plastic, where the band may be sized to fit the user's ring finger or the ring may be provided with a flexible shape or biasing mechanism to similarly fit the user's finger in a snug fit.

The width $W_{12}$ of the band 12, measured from an outer front-facing side surface 26 of the band 12 to an outer rear-facing side surface 28 of the band, increases in a tapered fashion from a lower portion 30 of the band to an upper portion 32 of the band 12 adjacent to the display device 18. A thinner disposition at the expansion feature 24 enables easier stretching or flexing of the band 12 to accommodate different finger sizes while the thicker disposition upwards from the expansion feature 24 increases surface area of the band in contact with the user's finger. A snug fit at the user's finger is helpful to ensure that the ring device remains substantially stationary during use to enable consistent and complete data capture. Additionally, the relatively high coefficient of friction associated with the silicon material in contact with the user's skin helps to retain the position and orientation of the ring thereat.

Besides enabling better retention of the device at the user's finger, the thicker disposition towards the upper portion 32 of the band 12 also accommodates the display device 18. At an upper portion 32 of the outer surface 20 of the finger band 12 is the display device 18, providing a display to the user of data (blood oxygen level and heart rate), the time, battery level of the device, or any other desired information. The display device 18 includes a display screen 34 received at a display housing and a human machine interface (HMI) button 36 that allows user inputs to control the device 10, such as to indicate the beginning and/or end of a sleep event or control settings of the band device. Optionally, the display screen 34 can be a touch screen and the HMI can be integrated into the touchscreen display. The display device 18 is coupled to the upper portion 32 of the band, such as via a connector portion 38 of the band 12 or the display device 18 can be integrally molded with the flexible material of the band 12 itself.

The display device 18 may also house the ECU 24, which includes electronic circuitry (such as on a printed circuit board (PCB)) and associated software and a battery to power the ring device 10. The ECU is in communicative connection with the pulse oximetry sensor 14, receives sensor data captured by the pulse oximetry sensor 14, and includes data processing hardware 24*a* for processing data captured by the sensor and received by the ECU, a storage unit 24*b* (i.e., memory hardware) for storing the data received from the sensor and processed by the data processor, and a transmitter 24*c* for communicating the data stored in the storage unit to a remote device. In the illustrated embodiment, the transmitter wirelessly transmits the stored data (such as via wifi, BLUETOOTH™ or other wireless protocol over a wireless network) to the remote device, but the transmitter may additionally or alternatively communicate the stored data through a wired connection.

Disposed at an outer front-facing side surface 26 of the finger band 12 is a charging port 39, covered by a charging port cover 40, for receiving a charging cord (such as a micro-USB) attached to a remote power supply to charge the battery that powers the ring device. The charging port 39 may be in communication with the transmitter of the ECU and thus a charging cord attached at the charging port may also function as a communication cord carrying transmitted data from the transmitter to the remote device. The charging port cover 40 may be made from the same flexible silicon material as the finger band 12 (and may be integrally molded with the band). The charging port cover 40 inserts and/or covers the charging port to prevent water or dust from entering the charging port during use. The charging port cover 40 also provides a smooth contact surface at the charging port to prevent irritating or harmful contact between the charging port and the user wearing the ring device 10.

Figure 2:
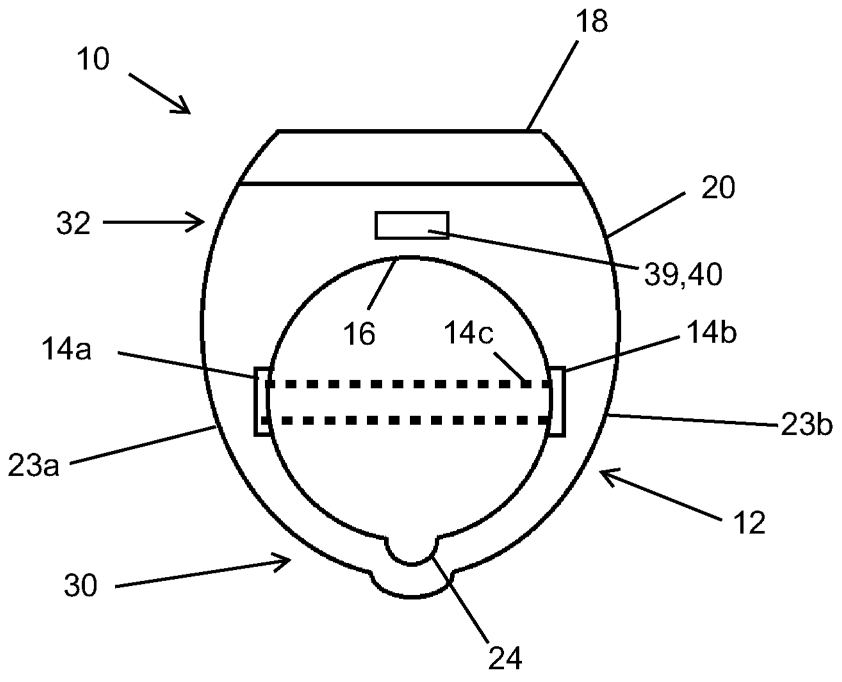
FIG. 2 is a side plan view of the wearable ring device of FIG. 1A.

Referring now to FIG. 2, an elevation view of the ring device 10 is shown. Disposed at and/or integrally molded with the inner surface 16 of the finger band is the pulse oximetry sensor 14 for collecting data representative of a user's blood oxygen level ($SpO_2$) and heart rate. The pulse oximetry sensor 14 is a transmission pulse oximeter and thus includes a light emitter 14*a* (such as an infrared LED and/or a red LED) at one side of the inner surface 16 of the band and a light detector 14*b* (such as photodiodes arranged to receive the transmitted light from the respective infrared and red LEDs) on the opposite side of the opening 22 (e.g., diametrically opposed) of the band 12. The light emitter 14*a* and light detector 14*b* are positioned directly across the opening 22 from one another at the inner surface 16 of the band 12 so that light passes from the light emitter 14*a* through the finger of the user to the light detector 14*b* on the other side of the user's finger. Dashed lines show the approximate light transmission path 14*c* from the light emitter 14*a* to the light detector 14*b*. In the illustrated embodiment, the light emitter 14*a* and light detector 14*b* are positioned 180 degrees away from each other along the circumference of the inner surface 16 of the band such that the light transmission path 14*c* extends along a radial direction relative to the center of the opening 22. Although shown at left-most and right-most positions at the inner surface, the light emitter and light detector can be located at any suitable position, such as top-most and south-most positions. The pulse oximetry sensor 14 communicates with the ECU and transmits sensor readings representative of the user's blood oxygen level and heart rate to the ECU. The pulse oximetry sensor 14 communicates with the ECU in any suitable fashion, such as wirelessly or via wired connections encased by the material of the band.

When placed on the finger of a user, the wearable band device 10 may automatically sense that it is being worn by a user (such as via contact sensors 35 at the inner surface of the band). For example, as shown in FIG. 1A, the sensors 14, 35, 37 of the band device 10 may comprise a sensor system 100, which measures one or more biometric parameters of a user and transmits corresponding biometric parameter data 102, 102*a*-102*c* to the ECU 24 for processing. Here, the biometric parameter data 102 may include pulse oximetry sensor data 102*a* measured by the pulse oximetry sensor 14, contact sensor data 102*b* measured by one or more of the contact sensors 35, and/or actimetry sensor data 37 measured by the actimetry sensor 37. When the band device 10 is powered on, the band device 10 may operate in a low-power standby mode during which the sensor system 100 is actively measuring for biometric parameters associated with a user. As shown in FIG. 1B, the ECU 24 may continuously monitor the sensor data 102 to determine whether the band device 10 is being worn by a user. For example, when the sensor data 102 exceeds a predetermined sensor data threshold $T_{102}$, the ECU 24 determines that the band device 10 is being worn by a user and, in response to such automatic sensing, begins recording data.

The band device records 10 pulse oximetry sensor data 102*a* at a time interval of at least every 2 seconds via the following method. The pulse oximetry sensor 14 transmits light from the light emitter 14*a* and detects the light that shines through the user's extremity via the light detector 14*b*. Signals generated by the pulse oximetry sensor 14, which correspond to a pulse oximetry measurement obtained by the pulse oximetry sensor 14, are transmitted to the data processor 24*a* of the ECU 24 as the pulse oximetry sensor data 102*a*. The ECU 24 processes the pulse oximetry sensor data 102*a* to determine the user's heart rate and blood oxygen level. The ECU 24 may also process the pulse sensor oximetry data 102*a*, as will be described further below, to determine a hypoxic burden, oxygen desaturation index (ODI) or apnea hypopnea index (AHI) of any apnea event detected during the sleep event. The processed data 104 is stored at the storage unit 24*b* of the ECU 24. This data collection process is repeated on a continuous basis or at a selected time interval, such as at least every 3 seconds, at least every 2 seconds, at least every 1 second, or an interval directly associated with the user's heartbeat (e.g., pulse oximetry sensor data 102*a* is collected at each heartbeat). In some examples, the time interval for collecting and recording data is between 1 and 2 seconds, between 0.8 and 1.8 seconds, between 0.5 and 1.5 seconds, between 0.8 and 2.2 seconds, between 0.5 and 2.5 seconds, or between 0.7 and 1.2 seconds.

In additional implementations, the time interval for data collection may be determined directly associated with the heart rate of the user. A person's blood oxygen level is most likely to change upon the occurrence of a heartbeat. In other words, when the heart beats, it pulses newly oxygenated blood throughout the body and thus, a user's blood oxygen level is unlikely to significantly change until the occurrence of the next heartbeat. Therefore, measurements of a person's blood oxygen level at two points in time between the subsequent heartbeats are likely to render substantially similar results. Triggering a measurement by the pulse oximetry sensor 14 of a user's blood oxygen level only upon the recognition of a heartbeat can ensure that each possible, useful data point is collected and unnecessary or duplicative data points are avoided.

The wearable band device 10 continues to read, process, and store the user's heart rate and blood oxygen levels (collectively "collect data 102") over the entire duration of the user's sleep event. When the user removes the device 10 from their extremity, the device may recognize that it is no longer being worn by the user (such as via contact sensors or responsive to no longer being able to read and collect data) and communicates the stored data to a remote device 8. The device 10 may have a built-in time interval delay (such as 10 or 30 seconds) between recognizing the end of a sleep event and transmitting the stored data to the remote device 8. This accommodates situations where the user may briefly remove and replace the band on their extremity without triggering the end of the sleep event and subsequent transmission of data to the remote device. The band device 10 communicates the collected data 102 via wifi, BLUETOOTH™ or over a wireless network or through a wired connection via the communications port 39.

Collection of data during a user's sleep event or overnight may be referred to as a session of data collection. The wearable band device 10 may transmit the entirety of data 102 collected and processed during the session at once after the session has ended (e.g., when the user removes the ring) or the device 10 may transmit data continuously or intermittently throughout the session. Storage capacity at storage unit 24 of the device 10 may allow for the device 10 to capture, process and simultaneously store several sessions' worth of data 102. For example, if a user is away from the remote device 8 with which they have paired their band device 10 but still wishes to collect several nights' worth of data 102. In those cases, the device 10 may recognize that it is out of range of the connected device 8 and thus incapable of transmitting the recently collected session worth of data 102. The device 10 then tags the stored data 102, 104 as not having been transmitted to the remote device 8. The device 10 may then upload several events or sessions' worth of data 102, 104 the next time it is able to connect to the remote device 8. Additionally or alternatively, the system may overwrite a previously collected session worth of data with data from a session currently being collected such as to recycle storage space on the device or ensure that only a single session of data is stored at any given time. The battery and storage capacity of the device 10 may enable data recording over several sessions, such as for 40 hours of data collection or more.

As indicated above, the device may communicate stored data to a remote device 8 after the user removes the band device 10 following a sleep event. Alternatively, the wearable band device may continuously communicate the processed and stored data to a remote device in a livestream mode. This may be beneficial in sleep study or other medical settings where it is desirable to continuously monitor a user's heart rate and blood oxygen levels while they sleep (or remotely while they are awake). For example, the wearable band device 10 provides a more comfortable and more accurate alternative to uncomfortable and unreliable fingertip pulse oximeters frequently used in hospitals. These fingertip pulse oximeters are generally monitored remotely, such as at a nursing station, and can trigger alerts if a patient's blood oxygen level or heart rate falls out of a desired range. Fingertip pulse oximeters account for a significant number of false alerts, resulting in inefficiencies in patient care. Thus, replacement of fingertip pulse oximeters with the presently disclosed wearable band device would provide increased patient comfort and more reliable monitoring of patient blood oxygen levels and heart rate even outside of a sleep lab setting. Additionally, the user may wish to continuously track their own data levels, such as when using the device as an activity tracker or to monitor other waking health ailments.

After or during the data collection session, the device 10 may perform further processing, or advanced processing, on the collected pulse oximetry sensor readings beyond determining the user's heart rate and blood oxygen levels. Further processing may include determining the user's hypoxic burden in addition or in the alternative to other blood desaturation or sleep-apnea focused metrics. For example, other blood desaturation metrics may include the oxygen desaturation index (ODI), the average oxygen saturation for a sleep event, the nadir point for a night, the total sleep time less than 90% saturation (TST90), among other standard or non-standard oxygen saturation metrics. Because raw blood oxygen level readings are inherently noisy, it can be necessary to smooth the collected raw data. This may be done by time-averaging the blood oxygen ($SpO_2$) levels recorded over a several second period. Thus, a single value may be recorded for that several-second interval. This data smoothing method is adequate for monitoring slow blood oxygen level changes, but inadequate for measuring the transient changes that may occur and are necessary to monitor during apnea events. Instead, hypoxic burden smooths the signal using the ensemble average of oxygenation levels measured over a time period, which helps precisely identify the inflection points of transient apnea events.

The ensemble averaged oxygenation levels are tracked on a graph (such as seen in FIGS. 5-9) with the hypoxic burden defined as the area under the curve relative to an oxygenation baseline. For example, referring to FIG. 6, graph **60*b* comparing blood oxygen readings taken using the currently disclosed device (labeled "Ring Device") and a fingertip pulse oximeter device (labeled as "Spike") is shown. An oxygenation baseline may be determined to be a blood oxygen saturation level of 95%. In that case, the hypoxic burden of sleep apnea events, such as that represented by dip 62*b*, can be calculated as the area between the tracked chart of oxygenation readings collected using the presently disclosed device and a horizontal line at the 95 percent value. Thus, hypoxic burden calculations would be heavily influenced by duration, severity, and frequency of apnea events. It can be seen by the differences in areas covered by the respective "Spike" and "Ring Device" dips 62*b* that accuracy of hypoxic burden calculations rely heavily on the accuracy and sensitivity of the blood oxygen level readings. The spikes may also be confirmed by monitoring or overlaying heart rate measurements, which can often surge after an apnea event. When the remote device (such as a mobile phone or personal computer or wireless network) receives the collected and processed data, the data may have undergone advanced processing at the ECU of the wearable band device 10 or an ECU of the remote device 8** may perform the advanced processing.

Over an extended period of time and after the device 10 has collected and processed data from several sleep events, the collected data (including hypoxic burden or ODI) may be compared to historical data for that particular user to aid in tailoring the user's medication dosage. For example, a user taking medication may suffer from a similar number of sleep apnea events as before taking the medication, but the historical data and hypoxic burden may indicate that the user's apnea events have become less severe. This might indicate that the medication or device is working but requires a higher dosage. Other methods of detection might only recognize the same number of apnea events per sleep event and incorrectly indicate that the medication or device is not working. A user's data may also be compared to a database of other patients' data to compare reaction and effectiveness of medication relative to average outcomes.

Figure 3A:
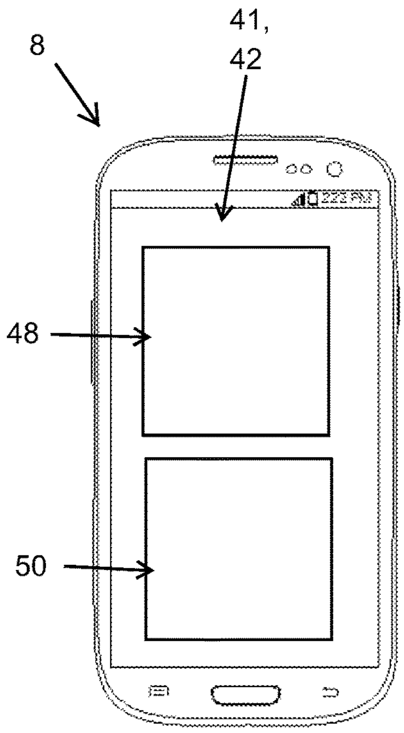
FIGS. 3A-3C are views of a smart phone application in use on a smart phone wirelessly connected to a finger ring pulse oximeter device.
Figure 3B:
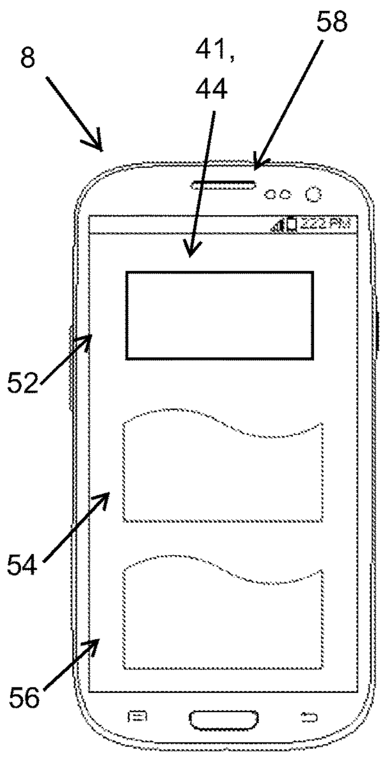
Figure 3C:
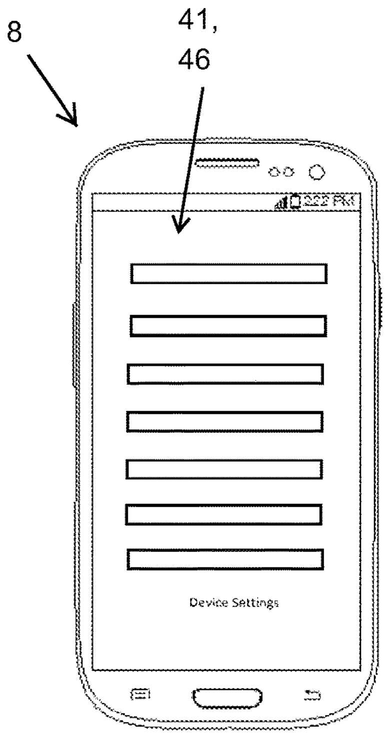

In reference to FIG. 3, the remote device 8 enables usage of a software application 41 associated with the wearable band device 10. The software application 41 supports such features as live stream monitoring of heart rate and blood oxygen levels via a dashboard 42 (FIG. 3A), review of data collected during a sleep event via a session page 44 (FIG. 3B), and the changing of settings of the wearable band device via user input within a settings page 46 of the application (FIG. 3C). For example, the dashboard 42 may allow a user to monitor their blood oxygen level 48 and heart rate 50 while wearing the device or from a particular point in time from a collected set of data. The session page 44 shows a summary of the blood oxygen level and heart rate data collected for a given sleep event on a given date. The summary includes a blood oxygen level chart 52, a heart rate chart 54, and a motion chart 56 over the same time period and a data table 58 that includes the following data points: time spent recording data during the sleep event, number of times that blood oxygen level dropped by 4% or greater, number of times the blood oxygen level dropped by 3% or greater, the average blood oxygen level of the user over the course of the sleep event, a calculated O2 score, an average heart rate over the course of the sleep event, the total time the user's blood oxygen saturation fell below 90%, the average number of drops in blood oxygen level per hour over the course of the sleep event, and the lowest recorded blood oxygen level during the sleep event. In additional examples, the software application 41 executing on the remote device 8 may calculate and display the hypoxic burden for a monitored event or session that uses the ensemble average of oxygenation levels measured over such a time period, so as to precisely identify more acute apnea events.

Settings adjustable via the mobile app (or optionally via user input at the display device) include blood oxygen level and heart rate reminders or alerts that trigger haptic feedback at the wearable band device if an apnea event is detected, if the user's oxygenation level drops below a certain threshold or if their heart rate falls out of a desired range. The alert may be in the form of haptic feedback or a sound or vibration of the mobile device to wake the user. The thresholds can be manually set by the user or responsive to historical data. These alerts may be turned off or made optional if instead it is desired to let the user sleep through the apnea event (or wake naturally due to the apnea event) to gather a more representative data set of the user's sleep cycles. The threshold can be set by the user, a doctor, or responsive to historical data. For example, if a user frequently suffers from mild sleep apnea events, the system may automatically set the haptic alarm to only trigger if a more severe apnea event with a lower dip in blood oxygen levels occurs. The user can also manage settings related to the strength of the ring device's haptic feedback, a screen mode and brightness for the ring device display screen. A user can also access software updates, reset their device, connect the wearable band device 10 to other mobile devices 8, and affect any other suitable settings related to the band device through the settings page in the mobile app.

To enable tracking of the user's motion, the wearable band device may include an actimetry sensor 37. Movement during sleep can be another indication of restless or interrupted sleep patterns, which can be useful as another data point in determining the efficacy of sleep apnea treatments. Actimetry sensors 37 measure the user's movement or actigraphy to also allow the ring device 10 to determine whether the user is asleep or awake, which can assist with calculating the total sleep time or duration of a sleep event. Further, the actimetry sensor 37 can provide functionality as an activity tracker. Blood oxygen levels and heart rates are important metrics in measuring athletic outputs so a more accurate and comfortable activity tracker according to the present disclosure can enable an athlete to better capture their performance during various workouts and activities beyond sleep events.

Figure 4:
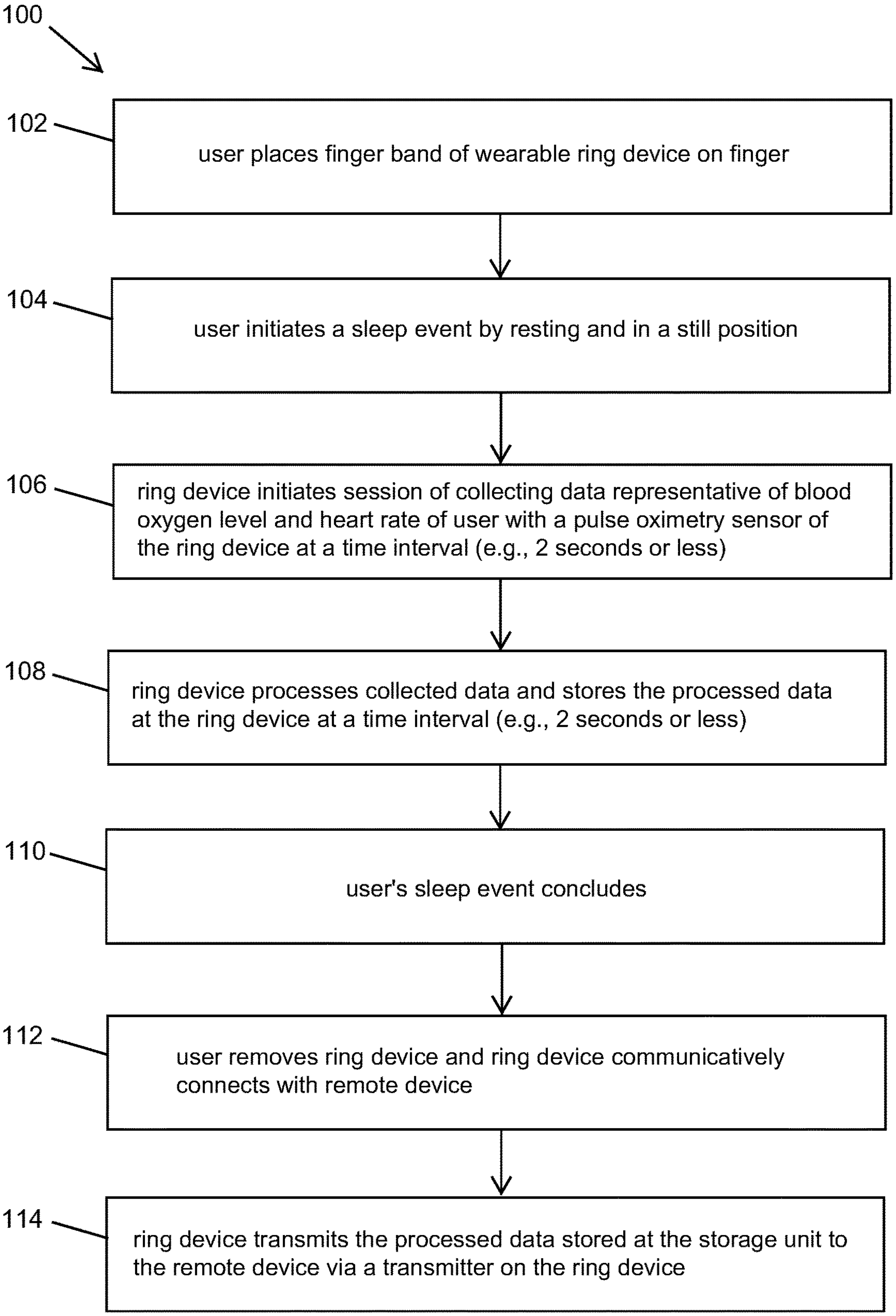
FIG. 4 is a flow chart showing an exemplary method for measuring health data with a wearable right device.

As shown for example in FIG. 4, a method 100 for measuring health data includes a user initially placing the band 12 of a wearable ring device 10 on a finger at step 102. The user then proceeds to initiate a sleep event at step 104, such as by resting and in a still position to fall asleep. While the finger band 12 is worn by the user during the sleep event, the method involves collecting data that is representative of the blood oxygen level and heart rate of the user at step 106. As describe above, collecting this data is done by the ECU receiving signals form the pulse oximetry sensor of the ring device at a time interval, such as every 2 seconds or less. At step 108, while the finger band is worn by the user during the sleep event and responsive to receiving the collected data at the ECU, the ECU processes the collected data via a data processor of the ECU and stores the processed data at a storage unit of the ECU. The ECU stores the processed data at a time interval, such as the same time interval that the data is received (e.g., every 2 seconds or less). At step 110, the sleep event concludes. Once the sleep event has concluded, the user may remove the wearable band device at step 112. In response to removing the band device and being in communication with a remote device, the band device at step 114 transmits the processed data stored at the storage unit to the remote device, such as via a transmitter of the ECU.

Figure 5:
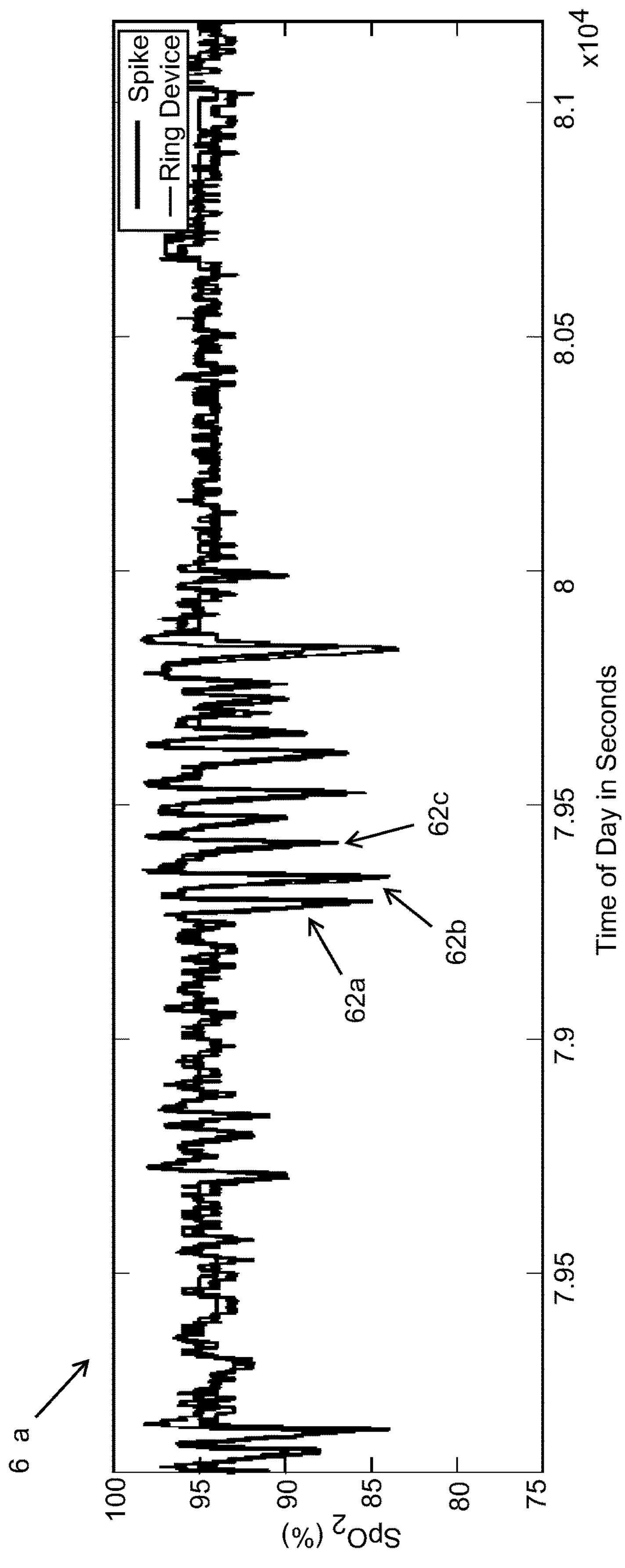
FIGS. 5 and 6 are graphs comparing readings of a user's blood oxygen level over time collected during multiple severe apnea events using a fingertip oximeter device and a finger ring oximeter device.
Figure 6:
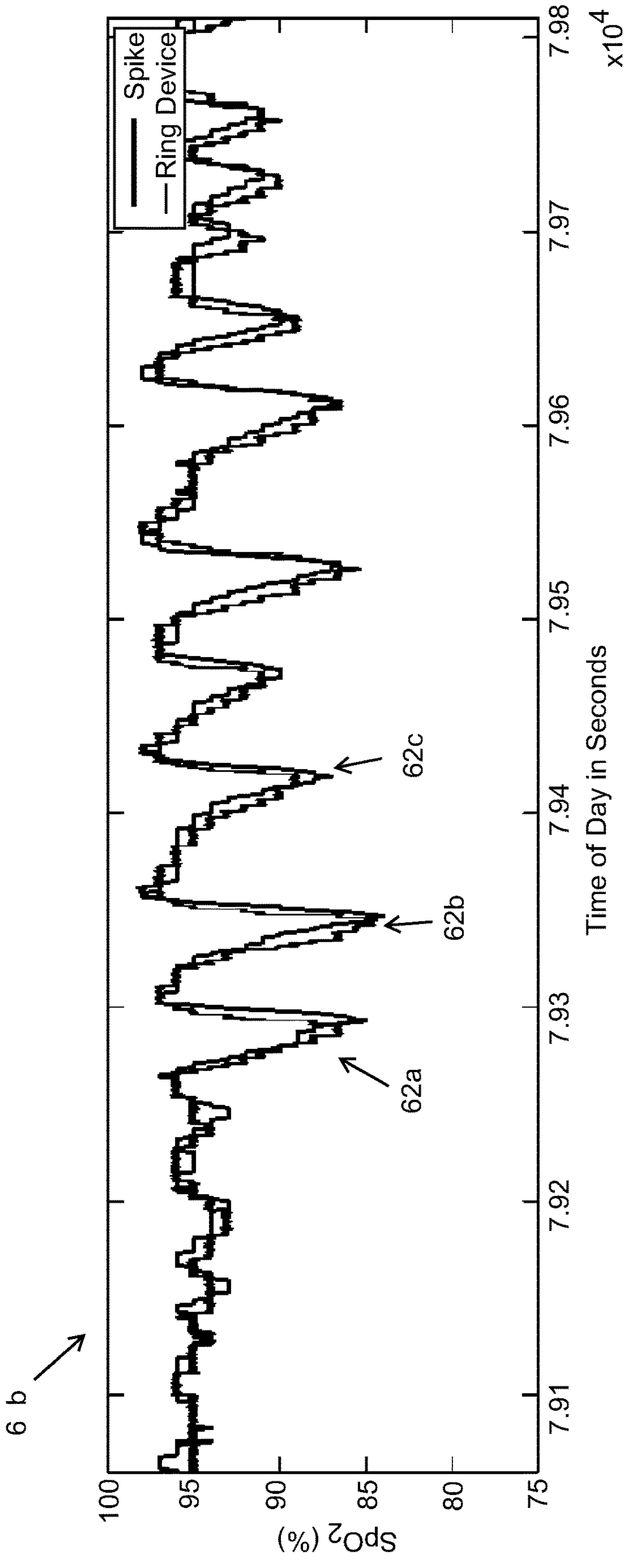
Figure 7:
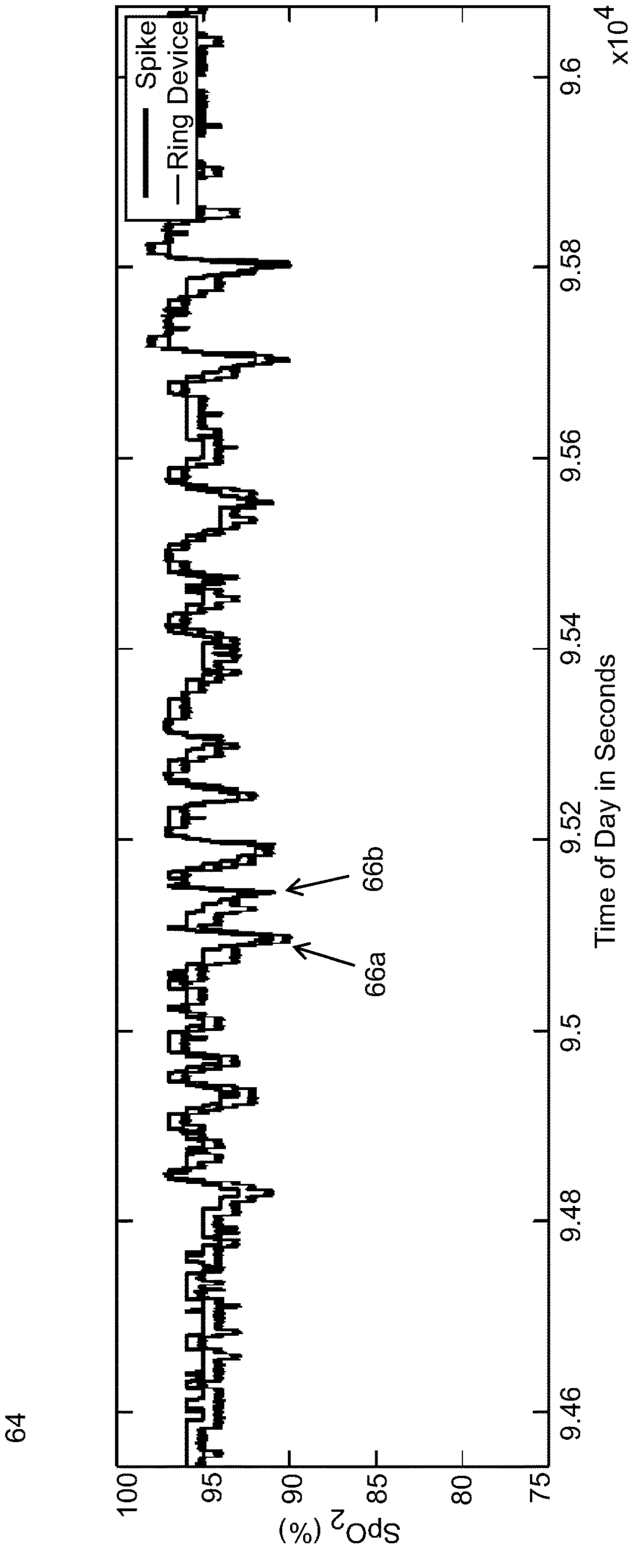
FIG. 7 is a graph comparing readings of a user's blood oxygen level over time collected during multiple mild apnea events using a fingertip oximeter device and a finger ring oximeter device.

Thus, the wearable band device 10 described herein enables greater user comfort and more accurate data collection. In reference to FIG. 5, a graph 60*a* comparing blood oxygen readings taken using the currently disclosed device (labeled "Ring Device") and a fingertip pulse oximeter device (labeled as "Spike") is shown. The two devices collected blood oxygen level readings from a user during a sleep event and registered some dips (such as dips 62*a*-62*c*) in oxygenation levels caused by apnea events. As shown by the graph 60*b* of FIG. 6, which compares the same two devices over a shorter period of time, the currently disclosed device 10 captures blood oxygen readings more frequently and thus can output smoother and more precise measurements. This results in more accurate calculations in the severity and length of apnea events experienced by a user. For example, compare the fingertip readings and finger ring readings during the apnea event represented by dip 62*c*, where the finger ring reading recognized a drop in oxygenation level at an earlier point in time and also registered a more precise minimum level of oxygenation during the apnea event compared to the fingertip reading during the same apnea event. These minute differences in readings can be critical in determining the efficacy of dosages or the severity and length of apnea events.

Where FIGS. 5 and 6 depicted more severe apnea events (where the user's blood oxygen levels approached and sometimes dipped below 85%), the graph 64 of FIG. 7 compares blood oxygen level readings for a user experiencing more mild apnea events (where the user's blood oxygen levels only dipped to about 90%). As seen between apnea events represented by dips 66*a* and 66*b*, the less frequent measurements of the fingertip device can result in measurements that indicate a user's blood oxygen level has not returned to a normal baseline following a dip. This can result in carryover or overlap in detected apnea events, where the separate, less severe apnea events may be registered as a single, longer apnea event or detection of an apnea event when one has not occurred (for example, if a user's dip in oxygenation level is due to common sleep habits such as slow, deep breaths or a reduced heart rate rather than an acute apnea event). These differences are critical in differentiating between normal sleep habits and the occurrence of mild or acute apnea events.

Figure 8:
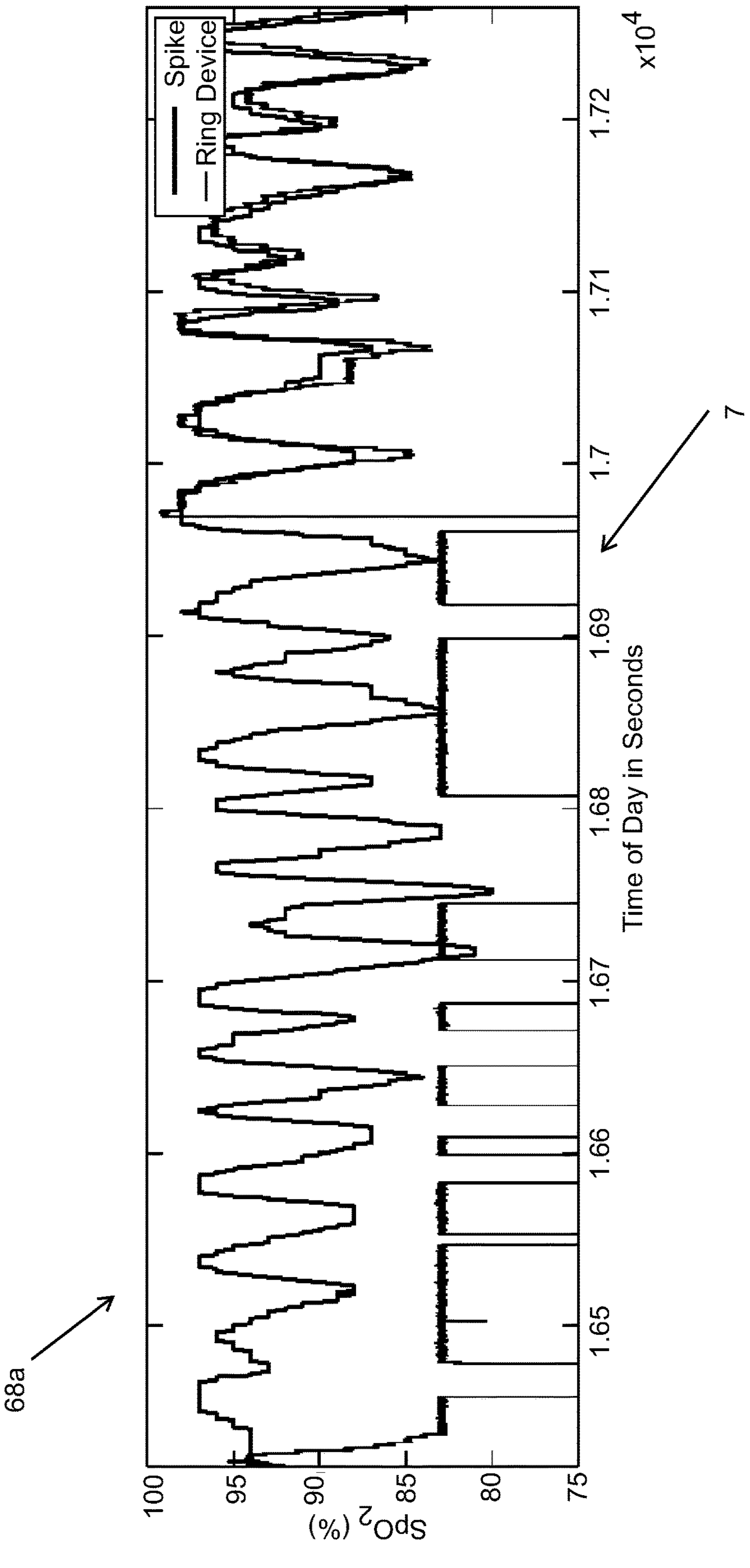
FIGS. 8 and 9 are graphs comparing readings of a user's blood oxygen level over time collected using a fingertip oximeter device and a finger ring oximeter device during events which caused the fingertip device to collect inaccurate readings.
Figure 9:
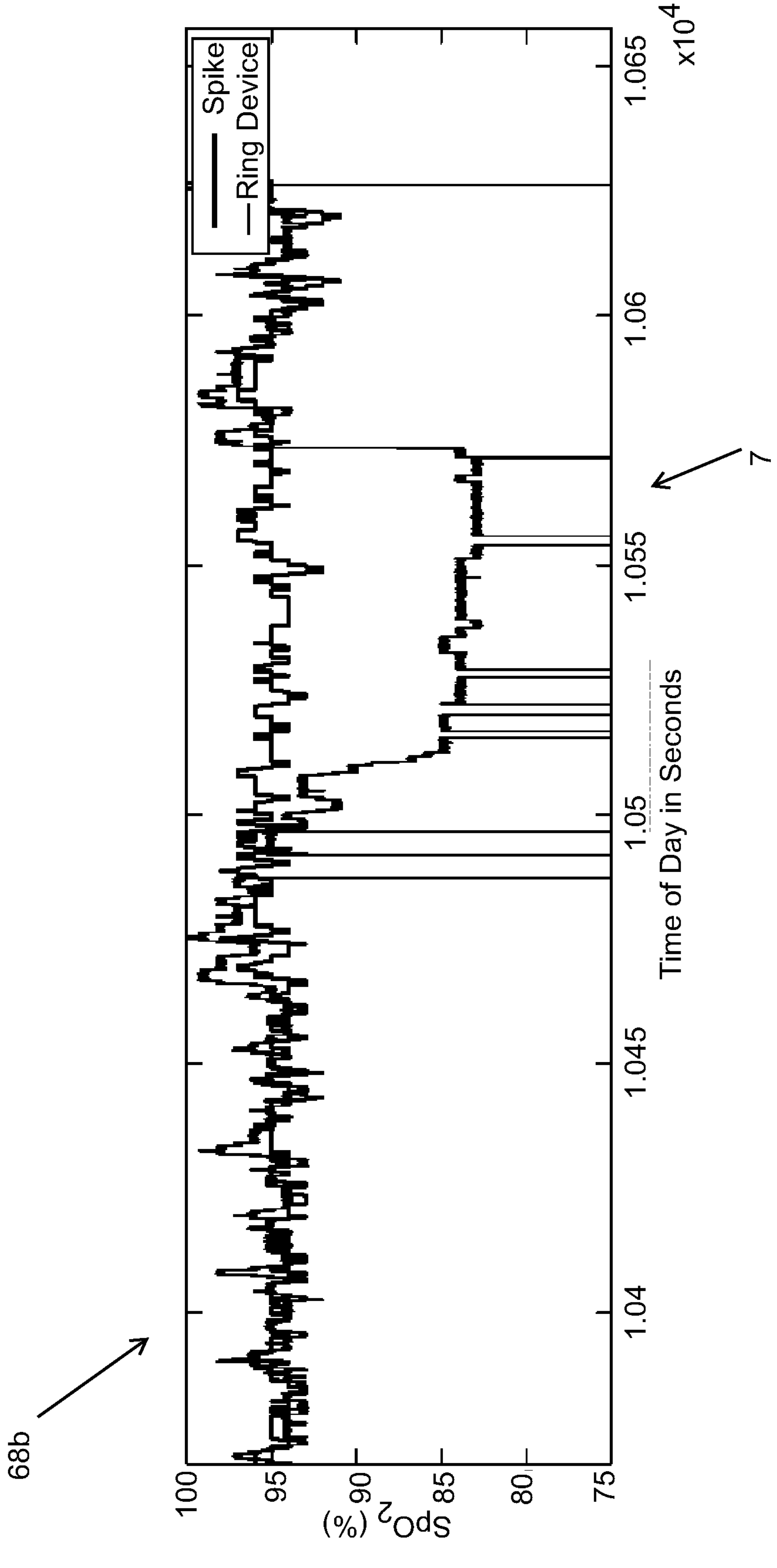

Referring to the graphs 68*a*, 68*b* of FIGS. 8 and 9, the presently disclosed wearable band device 10 continued to track blood oxygen levels of a user during an event 70 where the fingertip device was unable to gather accurate readings. This can occur if the fingertip device is shifted, falls off, or is taken off (due to discomfort) during use. As discussed above, the ring device is much more likely to remain worn throughout the duration of a sleep event because it is more comfortable and more secure at the user's finger.

Further, referring to the graph 72 of FIG. 10, the frequency of recording the oxygen saturation can significantly affect the accuracy of the detection of an apnea event. For example, recording oxygen saturation at a frequency of 0.25 Hz is not as accurate as recording oxygen saturation at a frequency of 1 Hz and can result in missed apnea events when patients with sleep apnea, such as shown at event 74 in FIG. 10. Specifically, the readings of a user's blood oxygen level taken at event 74 simultaneously with a fingertip oximeter device, a finger ring oximeter device recording oxygen saturation at a frequency of 0.25 Hz, and a finger ring oximeter device recording oxygen saturation at a frequency of 1 Hz clearly illustrates how the 1 Hz frequency (and fingertip oximeter device) registers the drop to approximately 92% $SpO_2$ for several readings or instances that are not recorded by the ring device measuring at a frequency of 0.25 Hz. Accordingly, the ring device may operate at such a frequency of greater than or approximately 1 Hz, at least greater than 0.25 Hz, or greater than 0.5 Hz, or greater than 0.75 Hz.

Thus, the present disclosure provides a wearable band device that collects blood oxygen and heart rate data via a transmission pulse oximetry sensor. The device collects data during a sleep event at a rapid time interval, such as every 2 seconds or less, processes the collected data and stores the processed data. The device provides more accurate readings than known pulse oximeter devices and provides more reliable retention of the sensor at the body of the user, thus providing an improved method of screening, detecting, monitoring, and analyzing blood oxygen levels and heart rates of users over extended periods of time, such as during sleep events.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature; may be achieved with the two components (electrical or mechanical) and any additional intermediate members being integrally formed as a single unitary body with one another or with the two components; and may be permanent in nature or may be removable or releasable in nature, unless otherwise stated.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional implementations that also incorporate the recited features. Numbers, percentages, ratios, or other values stated herein are intended to include that value, and also other values that are "about" or "approximately" the stated value, as would be appreciated by one of ordinary skill in the art encompassed by implementations of the present disclosure. A stated value should therefore be interpreted broadly enough to encompass values that are at least close enough to the stated value to perform a desired function or achieve a desired result. For example, the terms "approximately," "about," and "substantially" may refer to an amount that is within less than 5% of, within less than 1% of, within less than 0.1% of, and within less than 0.01% of a stated amount.

Further, it should be understood that any directions or reference frames in the preceding description are merely relative directions or movements. For example, the terms "upper," "lower," "right," "left," "rear," "front," "vertical," "horizontal," and derivatives thereof shall relate to the orientation shown in FIG. 1. However, it is to be understood that various alternative orientations may be provided, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Changes and modifications in the specifically described embodiments may be carried out without departing from the principles of the present invention, which is intended to be limited only by the scope of the appended claims as interpreted according to the principles of patent law. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A health monitoring system comprising:

a finger band comprising an inner surface configured to at least partially surround a finger of a user;

one or more sensors including a pulse oximetry sensor disposed at the inner surface of the finger band and configured to collect sensor data including pulse oximetry representative of a heart rate and a blood oxygen level of the user;

an electronic control unit (ECU) disposed at the finger band and connected to the pulse oximetry sensor, the ECU comprising electronic circuitry and associated software, and the electronic circuitry comprising a data processor, a storage unit, and a transmitter;

wherein the ECU is configured to determine the finger band is worn by the user based on data collected by the one or more sensors;

wherein the pulse oximetry sensor, responsive to the ECU determining the finger band is worn by the user during a sleep event, collects pulse oximetry data and transmits the collected pulse oximetry data to the ECU during the sleep event;

wherein the ECU, when the finger band is worn by the user during the sleep event, receives the collected pulse oximetry data from the pulse oximetry sensor, processes the collected pulse oximetry data with the data processor, and stores the processed pulse oximetry data in the storage unit at a time interval of every 3 seconds or less;

wherein the ECU stores the processed pulse oximetry data as a session of data collection that associates the processed pulse oximetry data with the sleep event;

wherein the ECU is configured to determine the finger band is removed from the user based on the collected sensor data;

wherein the ECU, responsive to determining the finger band is removed, determines the session of data collection has ended; and wherein the ECU, responsive to determining the finger band is removed from the user after the sleep event, transmits the session of data collection stored in the storage unit to a remote device via the transmitter for monitoring sleep apnea.

2. The health monitoring system of claim 1, wherein the pulse oximetry sensor comprises a light emitter for directing infrared and red wavelengths of light at the user and a light detector for receiving infrared and red wavelengths of light from the user.

3. The health monitoring system of claim 2, wherein the light emitter is disposed at a first location at the inner surface of the finger band and when electrically powered, directs a beam of light along radial path, and wherein the light detector is disposed at a second location at the inner surface of the finger band remote from the first location and within the radial path.

4. The health monitoring system of claim 1, wherein the pulse oximetry sensor collects the pulse oximetry data at a time interval of every 1 second or less.

5. The health monitoring system of claim 1, wherein the ECU is configured to trigger the pulse oximetry sensor to collect pulse oximetry data representative of the blood oxygen level of the user in response to collecting pulse oximetry data representative of a heartbeat of the user.

6. The health monitoring system of claim 1, wherein the ECU is configured to trigger the pulse oximetry sensor to collect the pulse oximetry data at a time interval associated with a calculated heart rate of the user.

7. The health monitoring system of claim 6, wherein the heart rate of the user comprises an average heart rate of the user.

8. The health monitoring system of claim 1, wherein the one or more sensors comprises a contact sensor configured to collect contact data and the sensor data includes the contact data.

9. The health monitoring system of claim 1, further comprising an actimetry sensor disposed at the finger band and configured to collect data representative of movement of the user.

10. The health monitoring system of claim 9, wherein the actimetry sensor, in response to the ECU determining the finger band is worn by the user, collects data representative of the movement of the user and transmits the collected data to the ECU during the sleep event, wherein the ECU, when the finger band is worn by the user during the sleep event, receives the collected data from the actimetry sensor and the pulse oximetry sensor, processes the collected data with the data processor, and stores the processed data in the storage unit.

11. The health monitoring system of claim 1, wherein the ECU wirelessly transmits the processed pulse oximetry data stored in the storage unit to the remote device.

12. The health monitoring system of claim 1, wherein the pulse oximetry sensor collects pulse oximetry data representative of the blood oxygen saturation at a frequency of greater than 0.50 Hz.

13. A method for measuring health data, the method comprising:

providing a finger band to be worn by a user during a sleep event and comprising (i) one or more sensors including a pulse oximetry sensor disposed at an inner surface of the finger band and (ii) an electronic control unit (ECU) connected to the pulse oximetry sensor;

determining, at the ECU, whether the finger band is worn by the user during the sleep event based on sensor data collected by the one or more sensors;

in response to determining the finger band is worn by the user during the sleep event, collecting pulse oximetry data representative of a blood oxygen level and a heart rate of the user via the pulse oximetry sensor at a time interval of every 3 seconds or less and transmitting the collected pulse oximetry data to the ECU;

while the finger band is worn by the user during the sleep event and responsive to receiving the collected pulse oximetry data at the ECU, processing the collected pulse oximetry data via a data processor of the ECU and storing the processed pulse oximetry data at a storage unit of the ECU;

storing the processed pulse oximetry data as a session of data collection that associates the processed pulse oximetry data with the sleep event;

determining, at the ECU, a conclusion of the sleep event based on the sensor data; and in response to determining the conclusion of the sleep event:

determining, at the ECU, the session of data collection has ended; and transmitting the session of data collection stored at the storage unit to a remote device via a transmitter of the ECU.

14. The method of claim 13, wherein the ECU is disposed at the finger band.

15. The method of claim 13, wherein the ECU is remote from the finger band.

16. The method of claim 15, wherein the ECU is disposed at the remote device.

17. The method of claim 13, wherein the ECU is configured to trigger the pulse oximetry sensor to collect pulse oximetry data representative of the blood oxygen level of the user at a time interval representative of the heart rate of the user.

18. The method of claim 13, wherein processing the collected pulse oximetry data comprises calculating a hypoxic burden value.

19. A health monitoring system comprising:

a wearable band device comprising an inner surface configured to at least partially surround an extremity of a user;

one or more sensors including a pulse oximetry sensor disposed at the inner surface of the wearable band device and comprising a light emitter for transmitting infrared and red wavelengths of light through the extremity of the user and a light detector for receiving the infrared and red wavelengths of light from the user;

an electronic control unit (ECU) electrically connected to the pulse oximetry sensor, the ECU comprising electronic circuitry and associated software, and the electronic circuitry comprising a data processor a storage unit;

wherein the ECU is configured to determine the wearable band device is worn by the user based on sensor data collected by the one or more sensors;

wherein the pulse oximetry sensor, in response to the ECU determining the wearable band device is worn by the user, collects pulse oximetry data representative of a heart rate and a blood oxygen level of the user during a sleep event and transmits the collected pulse oximetry data to the ECU during the sleep event;

wherein the ECU receives the collected pulse oximetry data from the pulse oximetry sensor, processes the collected pulse oximetry data with the data processor, and stores the processed data in the storage unit at a time interval of every 2 seconds or less;

wherein the ECU stores the processed pulse oximetry data as a session of data collection that associates the processed pulse oximetry data with the sleep event;

wherein the ECU is configured to determine the wearable band device is removed from the user based on the sensor data;

wherein the ECU, responsive to determining the wearable band is removed, determines the session of data collection has ended; and wherein, in response to determining the wearable band device is removed from the user, the session of data collection stored in the storage unit associated with the sleep event is processed by at least one of the ECU or a secondary device for detecting, diagnosing, or monitoring sleep apnea.

20. The health monitoring system of claim 19, wherein the light emitter is disposed at a first location at the inner surface of the wearable band device and when electrically powered, directs a beam of light along an radial path, and wherein the light detector is disposed at a second location at the inner surface of the wearable band device remote from the first location and within the radial path.

21. The health monitoring system of claim 19, wherein the pulse oximetry sensor collects pulse oximetry data representative of the heart rate and the blood oxygen level of the user at a time interval of every 1 second or less.

22. The health monitoring system of claim 19, wherein the ECU is configured to trigger the pulse oximetry sensor to collect the pulse oximetry data representative of the blood oxygen level of the user at a time interval representative of a calculated heart rate of the user.

23. The health monitoring system of claim 19, wherein the pulse oximetry sensor collects pulse oximetry data representative of the blood oxygen saturation at a frequency of approximately 1 Hz.

24. The health monitoring system of claim 19, wherein the one or more sensors comprises a contact sensor configured to collect contact data, and wherein the sensor data includes the contact data.

25. The health monitoring system of claim 19, wherein, in response to determining the wearable band device is removed from the user, the ECU transmits the collected pulse oximetry data stored in the storage unit to the secondary device via a transmitter.

26. The health monitoring system of claim 19, further comprising an actimetry sensor disposed at the wearable band device and configured to collect data representative of movement of the user.

27. The health monitoring system of claim 26, wherein the actimetry sensor, in response to the ECU determining the wearable band device is worn by the user, collects data representative of the movement of the user and transmits the collected data to the ECU during the sleep event, wherein the ECU, when the wearable band device is worn by the user during the sleep event, receives the collected data from the actimetry sensor and the pulse oximetry sensor, processes the collected data with the data processor, and stores the processed data in the storage unit.

28. The health monitoring system of claim 19, wherein the ECU wirelessly transmits the collected pulse oximetry data stored in the storage unit to the secondary device.

29. The health monitoring system of claim 19, wherein the wearable band device is configured to surround the extremity of the user, the extremity comprising a finger, a wrist, a forearm, an upper arm, an ankle, a leg, a foot or a toe.

* * * * *